US006409989B2

(12) United States Patent
Matianich et al.

(10) Patent No.: US 6,409,989 B2
(45) Date of Patent: Jun. 25, 2002

(54) INJECTABLE CARBON COMPOSITIONS IN STABLE AQUEOUS SUSPENSION; METHOD FOR PREPARING THEM AND METHOD OF PRESURGICAL MARKING IN THE INVESTIGATION OF NONPALPABLE MAMMARY PATHOLOGIES BY APPLYING SAID COMPOSITIONS

(75) Inventors: Pedro Humberto Arturo Matianich; Juliana Gabor, both of Buenos Aires (AR)

(73) Assignee: Laboratorios Temis Lostalo S.A. (AR)

( * ) Notice: Subject to any disclaimer, the term of this patent is extended or adjusted under 35 U.S.C. 154(b) by 4 days.

(21) Appl. No.: 09/731,336

(22) Filed: Dec. 6, 2000

Related U.S. Application Data

(62) Division of application No. 09/479,361, filed on Jan. 7, 2000, now abandoned.

(30) Foreign Application Priority Data

Jun. 28, 1999 (AR) .......................................... 990103112

(51) Int. Cl.$^7$ ........................ A61K 49/00; A61K 49/22; A61K 33/44; C01B 31/08
(52) U.S. Cl. ........................ 424/9.1; 424/9.8; 424/125; 424/489; 514/951; 514/952; 423/445 R; 423/460
(58) Field of Search .......................... 424/9.1, 9.8, 125, 424/489; 514/951, 952; 600/564, 565; 423/445 R, 460

(56) References Cited

U.S. PATENT DOCUMENTS 4,745,096 A * 5/1988 Keogh ........................ 502/413
5,422,330 A * 6/1995 Kaylor ........................ 502/402

OTHER PUBLICATIONS

Bonhomme–Faivre et al., "Formulation of a Charcoal suspension for Intratumor injection . . . " Pharmaceutical Research, vol. 14, No. 2, pp. 218–223, 1997.*
Kirk–Othmer Encyclopedia of Chemical Technology, 4$^{th}$ ed., John Wiley & Sons, New York, vol. 22, pp. 285–296, 1997.*
"Prebiopsy Localization of non–palpable breast cancer" by Dufrane et al. (1990).
"Investigation of Breast Abnormalities" by Svane et al; Ch. 6 in Screening Mammography, Breast Cancer diagnosis in Asymptomatic Women (1993).

* cited by examiner

Primary Examiner—John Pak
(74) Attorney, Agent, or Firm—Baker Botts LLP

(57) ABSTRACT

Injectable activated carbon suspensions are proposed for the presurgical marking of nonpalpable mammary pathologies for the purpose of achieving better diagnosis and treatment.

These are suspensions that flow freely and without the formation of obstructing aggregates in the needles used during their application, with carbon particles of micron granulometry limited to less than $50\mu$ and preferably between $2\mu$ and $6\mu$ in concentration of approximately 4.0% p/v in saline aqueous medium. A process is also proposed for preparing said compositions.

3 Claims, 1 Drawing Sheet

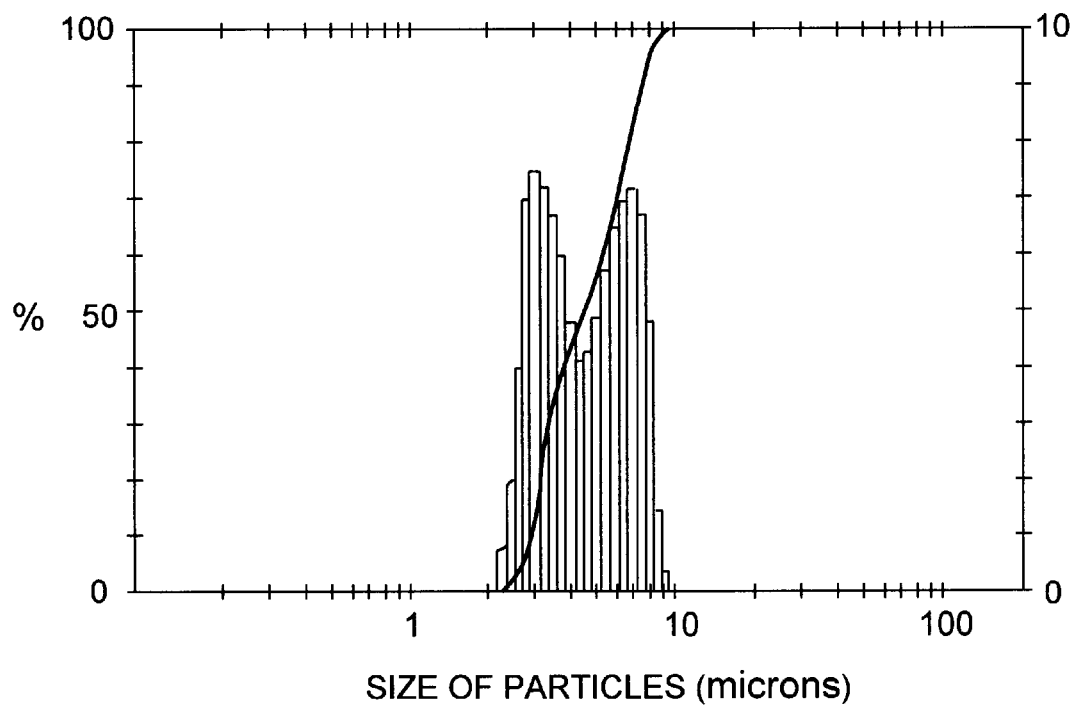
F I G. 1
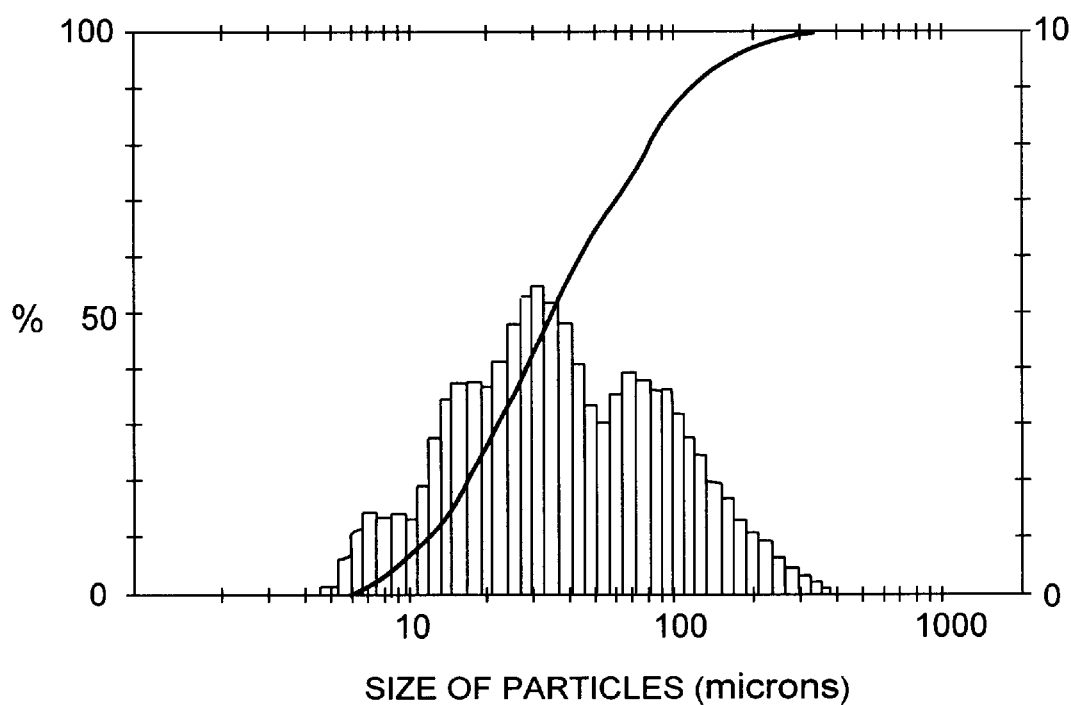
F I G. 2

INJECTABLE CARBON COMPOSITIONS IN STABLE AQUEOUS SUSPENSION; METHOD FOR PREPARING THEM AND METHOD OF PRESURGICAL MARKING IN THE INVESTIGATION OF NONPALPABLE MAMMARY PATHOLOGIES BY APPLYING SAID COMPOSITIONS

This is a divisional of application Ser. No. 09/479,361 filed Jan. 7, 2000 now abandoned.

The present invention relates to "carbon marking" of the breast for the purpose of localizing and delimiting histologically anomalous zones revealed by other techniques, such as echographic or radiographic, thus making possible more convenient and safer surgical access from the standpoint of precision of diagnosis and treatment and of aesthetic considerations with the mammary tissues undergoing surgery.

Among the presurgical techniques of delimitation of non-palpable mammary lesions, carbon marking forms part of the set of techniques whose application requires operating on the breast in minimally invasive form, for example, through the insertion of a needle to discharge the carbon in the zone investigated under radiographic or echographic monitoring.

Other techniques of this group include marking using wires bent at one of their ends (hooks or harpoons) which are inserted in the mammary tissue using a tubular piece for guiding and positioning in relation to the target (lesion) under radiographic monitoring. Another technique of said group involves the injection of organic dye solutions, such as methylene blue or toluidine blue, for purposes of demarcating the zone to be studied.

No method of presurgical demarcation of nonpalpable mammary lesions, whether noninvasive or minimally invasive, is free of defects: the noninvasive methods, which basically involve the use of measurements from reference points (the nipple, for example) and marking of the skin, raise the possibility of unreliable markings and the ultimate results entail the risk of either overly wide or incomplete exeresis, with the possibility in both cases of mammary disfiguration.

In the use of minimally invasive techniques, the risks are in relation to the nature of the instrument used. In the case of the hook, for example, although it is more precise than the previous technique, the instrument can possibly be displaced, with the formation of visible lesions, such as localized hemorrhages and hematomas.

Marking employing solutions of organic dyes like methylene blue or toluidine blue entails the need for rapid continuation of the diagnostic-therapeutic procedure, in view of the possibility of migration, diffusion and degradation of this type of dye.

The use of carbon in turn requires careful choice of the preparation, as to its granulometry (particle size) and needle gauge, in combination with a degree of skill in handling the injection device. All of these measures are aimed at preventing obstruction of the needle and promoting release of a continuous flow without interruptions, even in the course of extraction of the needle.

With respect to the latter technique (carbon marking), injectable suspensions of 4% carbon in an aqueous medium are used and they are administered by injection with needles in the order of 20 G.

This technique has met with quick acceptance thanks to its reduced cost and the overcoming of disadvantages usually present with other techniques, such as lack of precision, displacement of the marking instrument and rapid degradation, among other things. The use of carbon as presurgical marker, on the other hand, offers among its advantages prolonged permanence in the zone marked, with color and limits well differentiated and, not being radiopaque, neither the radiology of the specimen nor the histo-pathological examination of same being altered. Furthermore, suspensions of carbon particles in an aqueous medium are involved, which is physiologically appropriate.

The different techniques of presurgical localization of nonpalpable mammary lesions are described in the specialized bibliography (1) (2).

It is clear from what has been summarized in the foregoing text that presurgical mammary marking with aqueous carbon solutions is considered an extremely useful technique from the operational as well as economical standpoint, in spite of its possible limitations, such as obstruction of needles because of inadequate particle size and collapse or discontinuity of the discharge flow or stream.

This invention makes it possible to resolve the negative aspects mentioned by providing activated carbon suspensions of adequate particle size within precise limits, resulting in an operational improvement of the technique, being less difficult, more reliable and precise for the physician and more comfortable for the patient.

THE INVENTION

The main object of the present invention consists of injectable activated carbon solutions for the presurgical marking of mammary lesions, which comprise, in aqueous suspension, ground activated carbon having, all together, particles smaller than $50\mu$ in size and preferably between $2\mu$ and $6\mu$. Said compositions flow freely and without the formation of obstructing aggregates in the needles during their application.

The process of preparation of activated carbon of the aforementioned granulometry is also the object of the invention, useful for formulating said injectable compositions, preferably by grinding the activated carbon in a cylindrical rod mill, whose surface has a sufficient hardness for obtaining the effect desired, like, for example, those of zirconia ($ZrO_2$).

DETAILED DESCRIPTION OF THE INVENTION

Innovations in the art of preparing compositions for the presurgical marking of mammary lesions are combined in this invention, using aqueous suspensions of activated carbon as marker for identifying and delimiting the zone to be operated on, namely:

the selection of an optimum particle size of carbon for formulating compositions that flow freely and without the formation of obstructing aggregates in the needles used during their application;

the selection and relationship of the means making it possible to obtain and use activated carbon of that optimal particle size from the functional standpoint.

Said optimal particle size is clearly attainable according to this invention by processing the activated carbon preferably in roll (or rod) mills whose operating surface has sufficient hardness. Included within said range, among others, is zirconium oxide—zirconia ($ZrO_2$)—with a hardness of 1160 units on the Knoop Scale, which is preferably applicable as a component of the body or surface of said rods. The use of this type of mill is a preferred aspect of the present invention. Even more preferable is the combination of the grinding of activated carbon using said rods of zirconia (or coated with zirconia) in chambers or drums whose interior surface is polyurethane. With the combination of these two factors, grinding and abrasive surfaces of zirconia and polyurethane coating of the grinding chamber, the profile of distribution of particles sizes shown on the graph of FIG. 1 of injectable compositions for the presurgical marking of mammary lesions is obtained.

Other objects of the invention are: the methods for marking histologically abnormal mammary zones by injecting effective quantities of activated carbon of particle size less than $50\mu$, and preferably between $2\mu$ and $6\mu$, in aqueous suspension and dosage form used in said method.

BRIEF DESCRIPTION OF THE DRAWINGS

FIG. 1 corresponds to the graph of the profile of distribution of particle sizes of the injectable composition obtained in this invention, which was determined by using a Series 2600 Malvern Laser unit by the Laser Radiation Scattering method.

It is observed that the average value of $4.46\mu$ (D[v,0.5]) comes within the preferred range of $2\mu$ to $6\mu$, there being no particles with values higher than $50\mu$.

FIG. 2 corresponds to a graph similar to that of FIG. 1 of the injectable composition obtained without having undergone the grinding process, which was determined by using the same equipment described above.

It is observed that the average value of $31.85\mu$ (D[v,0.5]) is outside the preferred range of $2\mu$ to $6\mu$, particles existing with values higher than $50\mu$ (and even exceeding $300\mu$).

In the following example included by way of illustration, a preferred embodiment is described for obtaining activated carbon of granulometry conforming to the present invention.

DESCRIPTION OF THE MANUFACTURING PROCESS

1. In a stainless steel container of 5-lt capacity, equipped with means of stirring, place 1.2 lt of distilled water prefiltered through a membrane of $0.45\mu$ and depyrogenating plate.

2. Connect a helical agitator and add sodium chloride. Stir until dissolving it completely.

3. Add the surface-active agent and stir until dissolving it completely.

4. Add the activated carbon and stir until dispersing it completely.

5. Transfer the carbon suspension formed to an appropriate mill.

6. Grind for approximately 30 hours.

7. Place the ground suspension in a sterile glass vessel of 9-lt capacity and fill to 5 lt with distilled water filter through a $0.45\mu$ membrane and depyrogenating plate.

8. Stir for 15 minutes.

9. Fractionate in Class II neutral glass vial flasks to a proper volume.

10. Plug the flasks with butyl stoppers and aluminum auxiliary cover.

11. Sterilize in autoclave at 121° C. for 20 minutes.

What is claimed is:

1. A process for preparing activated carbon ground to a particle size not exceeding 50 $\mu$m for use in a free-flowing acqueous suspension for presurgical marking of mammary lesions, characterized in that a charge of activated carbon is ground for a period of from about 25 to about 60 hours in a cylindrical rod mill having a grinding chamber coated with a non-abrasive lining and containing rods.

2. Process in accordance with claim 1, further characterized in that said rods are made of ziconium oxide and the grinding chamber is coated with a polyurethane lining.

3. Process in accordance with claim 1, further characterized in that the grinding time is in the order of 30 hours.

* * * * *